United States Patent [19]

Santini, Jr. et al.

[11] Patent Number: 6,123,861
[45] Date of Patent: Sep. 26, 2000

[54] FABRICATION OF MICROCHIP DRUG DELIVERY DEVICES

[75] Inventors: John T. Santini, Jr., Jackson, Mich.; Michael J. Cima, Winchester; Robert S. Langer, Newton, both of Mass.

[73] Assignee: Massachusetts Institute of Technology, Cambridge, Mass.

[21] Appl. No.: 09/022,322

[22] Filed: Feb. 11, 1998

Related U.S. Application Data

[63] Continuation-in-part of application No. 08/675,375, Jul. 2, 1996, Pat. No. 5,797,898.

[51] Int. Cl.$^7$ ..................................................... C25F 7/00
[52] U.S. Cl. .................... 216/2; 216/39; 216/56
[58] Field of Search .................... 216/2, 39, 56; 604/890.1, 891.1, 93; 128/899

[56] References Cited

U.S. PATENT DOCUMENTS

| | | | |
|---|---|---|---|
| 3,692,027 | 9/1972 | Ellinwood | 604/891.1 |
| 4,003,379 | 1/1977 | Ellinwood | 604/891.1 |
| 4,146,029 | 3/1979 | Ellinwood | 604/891.1 |
| 4,360,019 | 11/1982 | Jassawalla | 604/131 |
| 4,507,115 | 3/1985 | Kambara et al. | 604/135 |
| 4,585,652 | 4/1986 | Miller et al. | 604/891.1 |
| 4,731,049 | 3/1988 | Parsi | 604/20 |
| 4,731,051 | 3/1988 | Fischell | 604/67 |

(List continued on next page.)

FOREIGN PATENT DOCUMENTS

| | | |
|---|---|---|
| WO 93/03790 | 3/1993 | WIPO . |
| WO 96/40420 | 12/1996 | WIPO . |
| WO 97/47370 | 12/1997 | WIPO . |
| WO 98/46325 | 10/1998 | WIPO . |

OTHER PUBLICATIONS

Bae, et al., "Pulsatile Drug Release by Electric Stimulus," *ACS Symposium Series* 545:98–110 (1994).

Bates, et al., "New Amorphous Thin–Film Lithium Electrolyte and Rechargeable Microbattery," *IEEE 35th International Power Sources Symposium* 337–339 (1992).

Jaeger, ed., "Introduction to Microelectronic Fabrication," vol. V, *Modular Series on Solid State Devices* (Addison–Wesley, Reading, MA, 1988).

*Primary Examiner*—Randy Gulakowski
*Assistant Examiner*—Anita Alanko
*Attorney, Agent, or Firm*—Arnall Golden & Gregory, LLP

[57] ABSTRACT

Fabrication methods are provided for microchips that control both the rate and time of release of multiple chemical substances and allow for the release of a wide variety of molecules in either a continuous or pulsatile manner. In all of the preferred embodiments, a material that is impermeable to the drugs or other molecules to be delivered and the surrounding fluids is used as the substrate. Reservoirs are etched into the substrate using either chemical (wet) etching or plasma (dry) etching techniques well known in the field of microfabrication. Hundreds to thousands of reservoirs can be fabricated on a single microchip using these techniques. A release system, which includes the molecules to be delivered, is inserted into the reservoirs by injection, inkjet printing, or spin coating methods. Exemplary release systems include polymers and polymeric matrices, non-polymeric matrices, and other excipients or diluents. The physical properties of the release system control the rate of release of the molecules. The reservoirs can contain multiple drugs or other molecules in variable dosages. The filled reservoirs can be capped with materials that passively disintegrate, materials that allow the molecules to diffuse passively out of the reservoir over time, or materials that disintegrate upon application of an electric potential. Release from an active device can be controlled by a preprogrammed microprocessor, remote control, or by biosensors.

13 Claims, 8 Drawing Sheets

U.S. PATENT DOCUMENTS

| | | |
|---|---|---|
| 4,793,825 | 12/1988 | Benjamin et al. .................... 604/891.1 |
| 4,994,023 | 2/1991 | Wellinghoff et al. ...................... 604/20 |
| 5,041,107 | 8/1991 | Heil, Jr. ................................ 604/891.1 |
| 5,042,975 | 8/1991 | Chien et al. ............................... 604/20 |
| 5,167,625 | 12/1992 | Jacobsen et al. .................... 604/891.1 |
| 5,170,801 | 12/1992 | Casper et al. ............................ 600/582 |
| 5,196,002 | 3/1993 | Hanover et al. ...................... 604/891.1 |
| 5,254,081 | 10/1993 | Maurer et al. ............................. 604/20 |
| 5,279,607 | 1/1994 | Schentag et al. .................... 604/890.1 |
| 5,318,557 | 6/1994 | Gross .................................. 604/891.1 |
| 5,336,213 | 8/1994 | D'Angelo et al. .................... 604/890.1 |
| 5,366,454 | 11/1994 | Currie et al. ......................... 604/890.1 |
| 5,368,588 | 11/1994 | Bettinger .............................. 604/891.1 |
| 5,368,704 | 11/1994 | Madou et al. ...................... 204/129.55 |
| 5,387,419 | 2/1995 | Levy et al. ............................... 424/422 |
| 5,443,508 | 8/1995 | Giampapa ................................ 623/11 |
| 5,490,962 | 2/1996 | Cima et al. ............................. 264/401 |
| 5,518,680 | 5/1996 | Cima et al. ............................. 264/401 |
| 5,651,900 | 7/1997 | Keller et al. .............................. 216/56 |
| 5,660,680 | 8/1997 | Keller ....................................... 438/50 |
| 5,770,076 | 6/1998 | Chu et al. ............................... 210/490 |
| 5,798,042 | 8/1998 | Chu et al. ............................... 210/490 |
| 5,830,659 | 11/1998 | Stewart ..................................... 435/6 |
| 5,893,974 | 4/1999 | Keller et al. .............................. 216/56 |
| 5,900,160 | 5/1999 | Whitesides et al. ...................... 216/33 |
| 5,938,923 | 8/1999 | Tu et al. ................................. 210/490 |
| 5,948,255 | 9/1999 | Keller et al. ....................... 210/321.84 |
| 5,962,081 | 10/1999 | Ohman et al. .............................. 216/2 |
| 5,985,328 | 11/1999 | Chu et al. ................................. 216/56 |
| 5,989,445 | 11/1999 | Wise et al. ............................... 216/62 |

OTHER PUBLICATIONS

Jones, et al., "Development and Performance of a Rechargeable Thin–Film Solid–State Microbattery," *J. Power Sources* 54:63–67 (1995).

Kwon, et al., "Electrically Erodible Polymer Gel For Controlled Release of Drugs," *Nature* 354:291–293 (1991).

Tierney, et al., "Electroreleasing Composite Membranes For Delivery of Insulin and Other Biomacromolecules," *J. Electrochem. Soc.* 137(6):2005–2006 (1990).

Tierney, et al., "New Electrorelease Systems Based on Microporous Membranes," *J. Electrochem. Soc.* 137(12):3789–3793 (1990).

Uhrich, et al., "Synthesis and Characterization of Degradable Poly(anhydride–co–imides), " *Macromolecules* 28:2184–2193 (1995).

Wolf, et al., "Silicon Processing for the VLSI Era," vol. 1—*Process Technology* (Lattice Press, Sunset Beach, CA 1986).

Tierney, M.J. et al, "New Electrorelease Systems Based On Microporous Membranes" J. Electrochem. Soc., vol. 137, No. 12, pp 3789–93, Dec. 1990.

RELEASE SYSTEM CONTAINING THE DRUG OR OTHER MOLECULE
 RESERVOIR CAP MATERIAL
 INSULATOR/ETCH MASK MATERIAL

DEGRADABLE RESERVOIR CAP MATERIAL

NON-DEGRADABLE RESERVOIR-CAP MATERIAL

DEGRADABLE RELEASE SYSTEM

NON-DEGRADABLE RELEASE SYSTEM

PURE DRUG OR OTHER MOLECULE (SOLID, LIQUID, OR GEL FORM)

INSULATOR/ETCH MASK MATERIAL

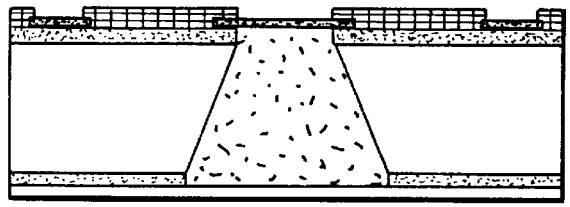
FIG. 8a
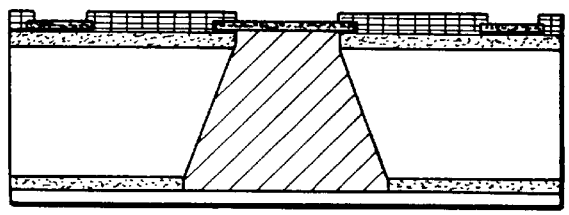
FIG. 8b
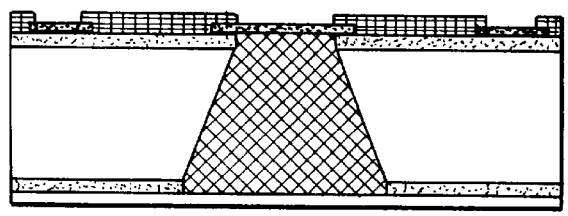
FIG. 8c
| | |
|---|---|
| 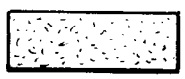 | INSULATOR / ETCH MASK MATERIAL |
|  | ANODE AND CATHODE MATERIAL |
|  | INSULATOR OVERLAYER |
|  | DEGRADABLE RELEASE SYSTEM |
|  | NON-DEGRADABLE RELEASE SYSTEM |
| 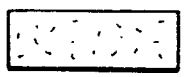 | PURE DRUG OR OTHER MOLECULE (SOLID, LIQUID, OR GEL FORM) |

FABRICATION OF MICROCHIP DRUG DELIVERY DEVICES

RELATED APPLICATIONS

This is a continuation-in-part of U.S. Ser. No. 08/675,375, filed Jul. 2, 1996, now U.S. Pat. No. 5,797,898 entitled "Microchip Drug Delivery Devices," by John T. Santini, Jr., Michael J. Cima, Robert S. Langer and Achim M. G öpferich.

FEDERALLY SPONSORED RESEARCH

Not applicable.

BACKGROUND OF THE INVENTION

This invention relates to miniaturized drug delivery devices and more particularly, to controlled time and rate release multi-welled drug delivery devices.

Drug delivery is an important aspect of medical treatment. The efficacy of many drugs is directly related to the way in which they are administered. Some therapies require that the drug be repeatedly administered to the patient over a long period of time. This makes the selection of a proper drug delivery method problematic. Patients often forget, are unwilling, or are unable to take their medication. Drug delivery also becomes problematic when the drugs are too potent for systemic delivery. Therefore, attempts have been made to design and fabricate a delivery device which is capable of the controlled, pulsatile or continuous release of a wide variety of molecules including, but not limited to, drugs and other therapeutics.

Controlled release polymeric devices have been designed to provide drug release over a period of time via diffusion of the drug out of the polymer and/or degradation of the polymer over the desired time period following administration to the patient. However, these devices are relatively simple.

U.S. Pat. No. 5,490,962 to Cima, et al. discloses the use of three dimensional printing methods to make more complex devices which provide release over a desired time frame, of one or more drugs. Although the general procedure for making a complex device is described, specific designs are not detailed.

U.S. Pat. No. 4,003,379 to Ellinwood describes an implantable electromechanically driven device that includes a flexible retractable walled container, which receives medication from a storage area via an inlet and then dispenses the medication into the body via an outlet. U.S. Pat. No. 4,146,029 and U.S. Pat. No. 3,692,027 to Ellinwood disclose self-powered medication systems that have programmable miniaturized dispensing means. U.S. Pat. No. 4,360,019 to Jassawalla discloses an implantable infusion device that includes an actuating means for delivery of the drug through a catheter. The actuating means includes a solenoid driven miniature pump. All of these devices include miniature power-driven mechanical parts that are required to operate in the body, i.e., they must retract, dispense, or pump. These are complicated and subject to breakdown. Moreover, due to complexity and size restrictions, they are unsuitable to deliver more than a few drugs or drug mixtures at a time.

Co-pending application U.S. Ser. No. 08/675,375, filed Jul. 2, 1996, discloses microchip devices for delivery of molecules, such as drugs. These devices typically include hundreds to thousands of reservoirs, or wells, containing the molecules and a release system that controls the rate of release of the molecules. For example, the reservoirs may have caps made of a material that degrades at a known rate or that has a known permeability (passive release). Alternately, the caps may include a conductive material capable of dissolving upon application of an electrical potential (active release).

It is therefore an object of the present invention to provide a method to manufacture a dependable, multi-welled delivery device for drugs and other molecules which can operate for weeks or years at a time.

It is another object of the present invention to provide a method to make a device that allows delivery of drugs or other molecules in either a pulsatile or continuous manner.

It is yet another object of the present invention to provide a method to make a device that allows the delivery to be controlled either passively or actively.

It is also an object of the present invention to provide a method to make a device that can hold many different drugs or other molecules of varying dosages and is small enough to be implanted, injected or swallowed, if desired.

SUMMARY OF THE INVENTION

Fabrication methods are provided for microchips that control both the rate and time of release of multiple chemical substances and allow for the release of a wide variety of molecules in either a continuous or pulsatile manner. Microchips are miniaturized devices constructed using methods commonly applied to the manufacture of integrated circuits, methods such as ultraviolet (UV) photolithography, reactive ion etching, and electron beam evaporation. The microchips provide control over the rate the molecules are released as well as the time at which release begins. The time of release can be controlled passively or actively.

In all of the preferred embodiments, a material that is impermeable to the drugs or other molecules to be delivered and the surrounding fluids is used as the substrate. Reservoirs are etched into the substrate using either chemical (wet) etching or plasma (dry) etching techniques well known in the field of microfabrication. Hundreds to thousands of reservoirs can be fabricated on a single microchip using these techniques. A release system, which includes the molecules to be delivered, is inserted into the reservoirs by injection, inkjet printing, spin coating methods, or other means. The device design makes it possible to fill the reservoirs with a release system in solid, liquid, or gel form. Exemplary release systems include polymers and polymeric matrices, non-polymeric matrices, and other excipients or diluents. The rate of release of the molecules is a function of the composition and structure of the release system. The reservoirs can contain multiple drugs or other molecules in variable dosages. Each of the reservoirs of a single microchip can contain different molecules and/or different amounts and concentrations, which can be released independently. The filled reservoirs can be capped with materials that passively disintegrate, materials that allow the molecules to diffuse passively out of the reservoir over time, or materials that disintegrate upon application of an electric potential. Release from an active device can be controlled by a preprogrammed microprocessor, remote control, or by biosensors.

In a preferred embodiment, the reservoir cap enables passive timed release, not requiring a power source, of molecules. The reservoirs are capped with materials that degrade or dissolve at a known rate or have a known permeability (diffusion constant) for the molecules to be delivered. Therefore, the degradation, dissolution or diffusion characteristics of the cap material determine the time at which the release of molecules in a particular reservoir begins. In effect, the microchip provides dual control of the release of molecules by selection of the release system (rate controller) and selection of the cap material (time controller, and in some cases, rate controller).

In another preferred embodiment, the reservoir cap enables active timed release, requiring a power source, of molecules. In this embodiment, the reservoir caps consist of a thin film of conductive material that is deposited over the reservoir, patterned to a desired geometry, and serves as an anode. Cathodes are also fabricated on the device with their size and placement dependent on the device's application and method of electric potential control. Conductive materials capable of dissolving into solution or forming soluble compounds or ions upon the application of an electric potential, including metals such as copper, gold, silver, and zinc and some polymers, are used in the active timed release device. When an electric potential is applied between an anode and cathode, the conductive material of the anode above the reservoir oxidizes to form soluble compounds or ions that dissolve into solution, exposing the release system containing the molecules to be delivered to the surrounding fluids. Alternatively, the application of an electric potential can be used to create changes in local pH near the anode reservoir cap to allow normally insoluble ions or oxidation products to become soluble. This would allow the reservoir cap to dissolve and expose the release system to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip. Activation of any reservoir can be achieved by preprogramming the microprocessor, by remote control, or by a signal from a biosensor.

DESCRIPTION OF THE DRAWINGS

FIGS. 8a–c are schematic views of several configurations of active delivery devices.

DETAILED DESCRIPTION

Figure 1:
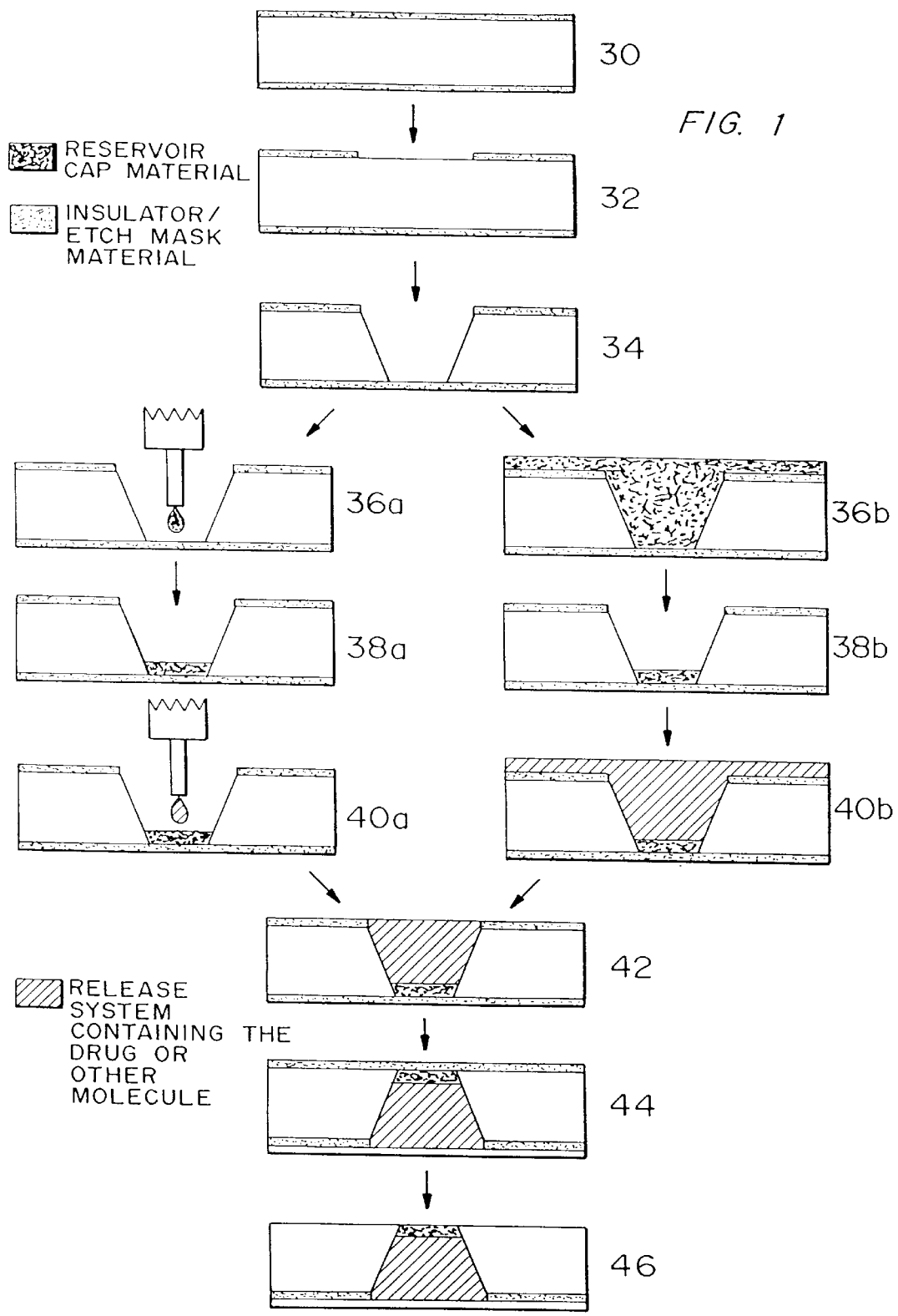
FIG. 1 depicts a typical fabrication scheme for a passive delivery device.

Microchip devices have been provided which can accurately deliver drugs and other molecules at defined rates and times according to the needs of the patient or other experimental system. As used herein, a "microchip" is a miniaturized device fabricated using methods commonly applied to the manufacture of integrated circuits such as ultraviolet (UV) photolithography, reactive ion etching, and electron beam evaporation, as described, for example, by S. Wolf and R. N. Tauber, *Silicon Processing for the VLSI Era, Volume 1—Process Technology*, Lattice Press, Sunset Beach, Calif., 1986; and R. C. Jaeger, *Introduction to Microelectronic Fabrication*, Volume V in the Modular Series on Solid State Devices, Addison-Wesley, Reading, Mass., 1988. The microchips provide control over the rate the molecules are released as well as the time at which release begins. The time of release can be controlled passively or actively. The microchip fabrication procedure allows the manufacture of devices with primary dimensions (length of a side if square or rectangular, or diameter if circular) ranging from less than a millimeter to several centimeters. A typical device thickness is 300 $\mu$m. However, the thickness of the device can vary from approximately 10 $\mu$m to several millimeters, depending on the device's application. Total device thickness and reservoir volume can also be increased by bonding or attaching additional silicon wafers or other substrate materials to the fabricated microchip device. In general, changing the device thickness affects the maximum number of reservoirs that may be incorporated onto a microchip and the volume of each reservoir. In vivo applications of the device would typically require devices having a primary dimension of 2 cm or smaller. Devices for in vivo applications are small enough to be swallowed or implanted using minimally invasive procedures. Smaller in vivo devices (on the order of a millimeter) can be implanted using a catheter or other injectable means. Devices for in vitro applications have fewer size restrictions and, if necessary, can be made much larger than the dimension ranges for in vivo devices.

MATERIALS FOR DEVICE FABRICATION

Each device consists of a substrate, reservoirs, and a release system containing, enclosing, or layered with the molecules to be delivered. Devices which control the release time of the molecules may include reservoir caps. Active devices may include control circuitry and a power source.

The Substrate

The substrate contains the etched or machined reservoirs and serves as the support for the microchip. Any material which can serve as a support, is suitable for etching or machining, and is impermeable to the molecules to be delivered and to the surrounding fluids, for example, water, blood, electrolytes or other solutions, may be used as a substrate. Examples of substrate materials include ceramics, semiconductors, and degradable and non-degradable polymers. Biocompatibility of the substrate material is preferred, but not required. For in vivo applications, non-biocompatible materials may be encapsulated in a biocompatible material, such as poly(ethylene glycol) or polytetrafluoroethylene-like materials, before use. One example of a strong, non-degradable, easily etched substrate that is impermeable to the molecules to be delivered and the surrounding fluids is silicon. In another embodiment, the substrate is made of a strong material that degrades or dissolves over a period of time into biocompatible components. This embodiment is preferred for in vivo applications where the device is implanted and physical removal of the device at a later time is not feasible or recommended, for example, brain implants. An example of a class of strong, biocompatible materials are the poly(anhydride-co-imides) discussed by K. E. Uhrich et al., "Synthesis and characterization of degradable poly(anhydride-co-imides)", *Macromolecules*, 1995, 28, 2184–93.

Release System

The molecules to be delivered may be inserted into the reservoirs in their pure form, as a liquid solution or gel, or they may be encapsulated within or by a release system. As used herein, "release system" includes both the situation where the molecules are in pure form, as either a solid or liquid, or are in a matrix formed of degradable material or a material which releases incorporated molecules by diffusion out of or disintegration of the matrix. The molecules can be sometimes contained in a release system because the degradation, dissolution or diffusion properties of the release system provide a method for controlling the release rate of the molecules. The molecules can be homogeneously or heterogeneously distributed within the release system. Selection of the release system is dependent on the desired rate of release of the molecules. Both non-degradable and degradable release systems can be used for delivery of molecules. Suitable release systems include polymers and polymeric matrices, non-polymeric matrices, or inorganic and organic excipients and diluents such as, but not limited to, calcium carbonate and sugar. Release systems may be natural or synthetic, although synthetic release systems are preferred due to the better characterization of release profiles. The release system is selected based on the period over which release is desired, generally in the range of at least three to twelve months for in vivo applications. In contrast, release times as short as a few seconds may be desirable for some in vitro applications. In some cases, continuous (constant) release from a reservoir may be most useful. In other cases, a pulse (bulk) release from a reservoir may provide more effective results. Note that a single pulse from one reservoir can be transformed into pulsatile release by using multiple reservoirs. It is also possible to incorporate several layers of a release system and other materials into a single reservoir to achieve pulsatile delivery from a single reservoir. Continuous release can be achieved by incorporating a release system that degrades, dissolves, or allows diffusion of molecules through it over an extended period of time. In addition, continuous release can be simulated by releasing several pulses of molecules in quick succession.

The release system material can be selected so that molecules of various molecular weights are released from a reservoir by diffusion out or through the material or degradation of the material. Biodegradable polymers, bioerodible hydrogels, and protein delivery systems are preferred for release of molecules by diffusion, degradation, or dissolution. In general, these materials degrade or dissolve either by enzymatic hydrolysis or exposure to water in vivo or in vitro, or by surface or bulk erosion. Representative synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include: poly(ethers) such as poly(ethylene oxide), poly(ethylene glycol), and poly(tetramethylene oxide); vinyl polymers—poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly(siloxanes); and any chemical derivatives thereof (substitutions, additions of chemical groups, for example, alkyl, alkylene, hydroxylations, oxidations, and other modifications routinely made by those skilled in the art), copolymers and mixtures thereof.

Molecules to be Released

Any natural or synthetic, organic or inorganic molecule or mixture thereof can be delivered. In one embodiment, the microchip is used to deliver drugs systemically to a patient in need thereof. In another embodiment, the construction and placement of the microchip in a patient enables the localized release of drugs that may be too potent for systemic delivery. As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. The drugs can be in the form of a single drug or drug mixtures and can include pharmaceutically acceptable carriers. In another embodiment, molecules are released in vitro in any system where the controlled release of a small (milligram to nanogram) amount of one or more molecules is required, for example, in the fields of analytic chemistry or medical diagnostics. Molecules can be effective as pH buffering agents, diagnostic agents, and reagents in complex reactions such as the polymerase chain reaction or other nucleic acid amplification procedures.

Reservoir Caps

In the passive timed release drug delivery devices, the reservoir caps are formed from a material that degrades or dissolves over time, or does not degrade or dissolve but is permeable to the molecules to be delivered. These materials are preferably polymeric materials. Materials can be selected for use as reservoir caps to give a variety of degradation rates or dissolution rates or permeabilities to enable the release of molecules from different reservoirs at different times and, in some cases, different rates. To obtain different release times (amounts of release time delay), caps can be formed of different polymers, the same polymer with different degrees of crosslinking, or a UV polymerizable polymer. In the latter case, varying the exposure of this polymer to UV light results in varying degrees of crosslinking and gives the cap material different diffusion properties or degradation or dissolution rates. Another way to obtain different release times is by using one polymer, but varying the thickness of that polymer. Thicker films of some polymers result in delayed release time. Any combination of polymer, degree of crosslinking, or polymer thickness can be modified to obtain a specific release time or rate. In one embodiment, the release system containing the molecules to be delivered is covered by a degradable cap material which is nearly impermeable to the molecules. The time of release of the molecules from the reservoir will be limited by the time necessary for the cap material to degrade or dissolve. In another embodiment, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays the onset of release. If diffusion through the cap material is limiting, the cap material determines the release rate of the molecules in addition to delaying the onset of release.

In the active timed release devices, the reservoir caps consist of a thin film of conductive material that is deposited over the reservoir, patterned to a desired geometry, and serves as an anode. Cathodes are also fabricated on the device with their size and placement dependent on the device's application and method of electric potential control. The anode is defined as the electrode where oxidation occurs. Any conductive material capable of dissolving into solution or forming soluble ions or oxidation compounds upon application of an electric potential can be used for the fabrication of the anodes and cathodes. In addition, materials that normally form insoluble ions or oxidation products in response to an electric potential can be used if, for example, local pH changes near the anode cause these oxidation products to become soluble. Examples of suitable reservoir cap materials include metals such as copper, gold, silver, and zinc, and some polymers, as described, for example, by I. C. Kwon et al., "Electrically erodible polymer gel for controlled release of drugs", *Nature,* 1991, 354, 291–93; and Y. H. Bae et al., "Pulsatile drug release by electric stimulus", *ACS Symposium Series,* 1994, 545, 98–110.

Device Packaging, Control Circuitry, and Power Source

Microelectronic device packages are typically made of an insulating or dielectric material such as aluminum oxide or silicon nitride. Their purpose is to allow all components of the device to be placed in close proximity and to facilitate the interconnection of components to power sources and to each other. For in vivo applications of the delivery device, the entire package, including all components (i.e. the device, the microprocessor, and the power source), are coated or encapsulated in a biocompatible material such as poly (ethylene glycol) or polytetrafluoroethylene-like materials. The materials requirements for in vitro applications may be less stringent and depend on the particular situation.

The control circuitry consists of a timer, a demultiplexer, a microprocessor, and an input source, for example, a memory source, a signal receiver, or a biosensor. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the delivery device. Selection of a source of input to the microprocessor such as memory sources, signal receivers, or biosensors depends on the delivery device's particular application and whether device operation is preprogrammed, controlled by remote means, or controlled by feedback from its environment (i.e. biofeedback).

The criteria for selection of a power source are small size, sufficient power capacity, ability to be integrated into the control circuitry, the ability to be recharged, and the length of time before recharging is necessary. Several lithium-based, rechargeable microbatteries have been described by S. D. Jones and J. R. Akridge, "Development and performance of a rechargeable thin-film solid-state microbattery", *Journal of Power Sources,* 1995, 54, 63–67; and J. B. Bates et al., "New amorphous thin-film lithium electrolyte and rechargeable microbattery", *IEEE 35$^{th}$ International Power Sources Symposium,* 1992, 337–39. These batteries are typically only ten microns thick and occupy 1 cm$^2$ of area. One or more of these batteries can be incorporated directly onto the delivery device.

METHODS OF DEVICE FABRICATION

Fabrication of the Reservoirs

Devices are manufactured using methods known to those skilled in the art, reviewed, for example, by Wolf et al. (1986) and Jaeger (1988).

Figure 2:
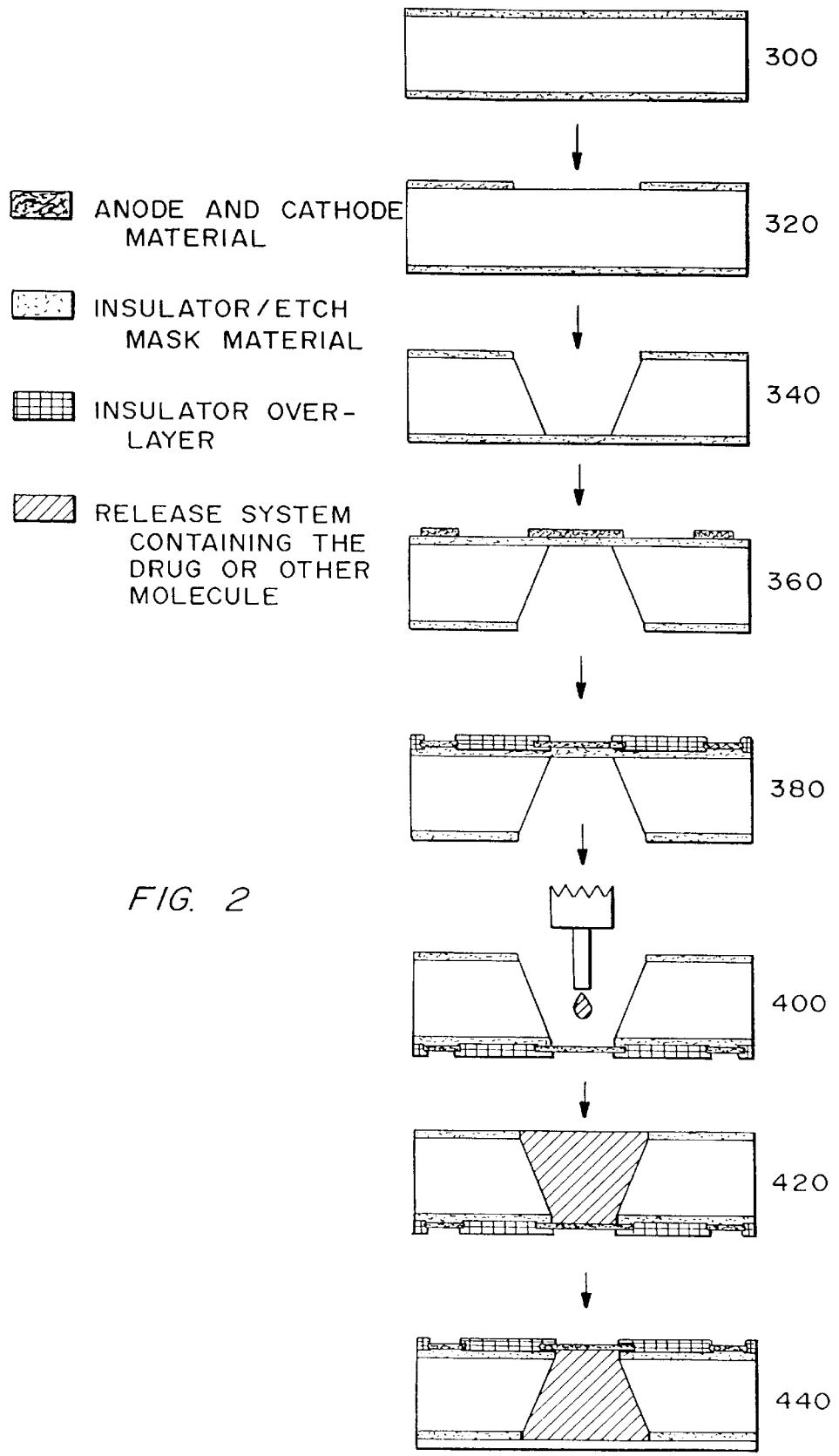
FIG. 2 depicts a typical fabrication scheme for an active delivery device.

In a preferred method of microchip manufacture, depicted in FIGS. 1 and 2, passive and active devices, respectively, fabrication begins by depositing and photolithographically patterning a material, typically an insulating or dielectric material, onto the substrate to serve as an etch mask during reservoir etching. Typical insulating materials for use as a mask include silicon nitride, silicon dioxide, and some polymers, such as polyimide. In a preferred embodiment, a thin film (approximately 1000–3000 Å) of low stress, silicon-rich nitride is deposited on both sides of a silicon wafer 30/300 in a Vertical Tube Reactor (VTR). Alternatively, a stoichiometric, polycrystalline silicon nitride ($Si_3N_4$) can be deposited by Low Pressure Chemical Vapor Deposition (LPCVD), or amorphous silicon nitride can be deposited by Plasma Enhanced Chemical Vapor Deposition (PECVD). Reservoirs are patterned into the silicon nitride film on one side of the wafer 32/320 by ultraviolet photolithography and either plasma etching or a chemical etch consisting of hot phosphoric acid or buffered hydrofluoric acid. The patterned silicon nitride serves as an etch mask for the chemical etching of the exposed silicon 34/340 by a concentrated potassium hydroxide solution (approximately 20–40% KOH by weight at a temperature of 75–90° C.). Alternatively, the reservoirs can be etched into the substrate by dry etching techniques such as reactive ion etching or ion beam etching. These techniques are commonly used in the fabrication of microelectronic devices, as reviewed, for example, by Wolf et al. (1986) and Jaeger (1988). Use of these microfabrication techniques allows the incorporation of hundreds to thousands of reservoirs on a single microchip. The spacing between each reservoir depends on its particular application and whether the device is a passive or active device. In a passive device, the reservoirs may be less than one micron apart. In an active device, the distance between the reservoirs may be slightly larger (between approximately 1 and 10 $\mu$m) due to the space occupied by the electrodes on or near each reservoir. Reservoirs can be made in nearly any shape and depth, and need not pass completely through the substrate. In a preferred embodiment, the reservoirs are etched into a (100) oriented, silicon substrate by potassium hydroxide, in the shape of a square pyramid having side walls sloped at 54°, and pass completely through the substrate (approximately 300 $\mu$m) to the silicon nitride film on the other side of the substrate, forming a silicon nitride membrane. (Here, the silicon nitride film serves as a potassium hydroxide etch stop.) The pyramidal shape allows easy filling of the reservoirs through the large opening of the reservoir (approximately 500 $\mu$m by 500 $\mu$m) on the patterned side of the substrate, release through the small opening of the reservoir (approximately 50 $\mu$m by 50 $\mu$m) on the other side of the substrate, and provides a large cavity inside the device for storing the drugs or other molecules to be delivered.

Fabrication of Passive Timed Release Reservoir Caps

In the fabrication of passive timed release microchips, the reservoir cap material is injected with a micro-syringe 36a, printed with an inkjet printer cartridge, or spin coated 36b into a reservoir having the thin membrane of insulating mask material still present over the small opening of the reservoir. If injection or inkjet printing methods are used, cap formation is complete after the material is injected or printed into the reservoir 38a and does not require further processing. If spin coating is used, the cap material is planarized by multiple spin coatings 36b. The surface of the film is then etched by a plasma, an ion beam, or chemical etchant until the desired cap thickness is obtained 38b. In a preferred embodiment, the insulating material used is silicon nitride and the cap material is printed into the reservoir with an inkjet cartridge filled with a solution or suspension of the cap material.

Reservoir caps control the time at which molecules are released from the reservoirs. Each reservoir cap can be of a different thickness or have different physical properties to vary the time at which each release system containing the molecules is exposed to the surrounding fluids. Injection, inkjet printing, and spin coating are the preferred methods of reservoir filling and any of these methods may be used to fill reservoirs, regardless of the reservoir's shape or size. However, injection and inkjet printing are the preferred methods of filling deep (greater than 10 μm) reservoirs or reservoirs with large openings (greater than 100 μm). For example, to obtain different cap thicknesses using injection or inkjet printing, different amounts of cap material are injected or printed directly into each individual reservoir. Spin coating is the preferred method of filling shallow (less than 10 μm) reservoirs, reservoirs that do not pass completely through the substrate, or reservoirs with small (less than 100 μm) openings. Variation in cap thickness or material by spin coating can be achieved by a repeated, step-wise process of spin coating, masking selected reservoirs, and etching. For example, to vary cap thickness with spin coating, the cap material is spin coated over the entire substrate. Spin coating is repeated, if necessary, until the material is nearly planarized. A mask material such as photoresist is patterned to cover the cap material in all the reservoirs except one. Plasma, ion beam, or chemical etchants are used to etch the cap material in the exposed reservoir to the desired thickness. The photoresist is then removed from the substrate. The process is repeated as a new layer of photoresist is deposited and patterned to cover the cap material in all the reservoirs except one (the exposed reservoir is not the same one already etched to its desired thickness). Etching of the exposed cap material in this reservoir continues until the desired cap thickness is obtained. This process of depositing and patterning a mask material such as photoresist, etching, and mask removal can be repeated until each reservoir has its own unique cap thickness. The techniques, UV photolithography, plasma or ion beam etching, etc., are well known to those skilled in the field of microfabrication.

Although injection, inkjet printing and spin coating are the preferred methods of cap fabrication, it is understood that each reservoir can be capped individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

Once a cap fabrication method is selected, additional methods for controlling the time of release of molecules from a reservoir can be utilized, for example, including either UV polymerizable polymers or the layering of release system and cap materials. In the first embodiment, where the reservoir caps are made of either an injected, inkjet printed or spin coated UV polymerizable polymer, each cap can be exposed to a different intensity of UV light to give varying degrees of crosslinking and therefore, different degradation or dissolution rates for degradable caps or different permeabilities to the molecules for non-degradable caps. Second, layers of cap material, both degradable and non-degradable, can be inserted between layers of the release system containing the molecules to be delivered by injection, inkjet printing, spin coating, or selective crosslinking. These and other similar methods allow complex release profiles (e.g., pulsatile delivery at irregular time intervals) to be achieved from a single reservoir.

If desired, a passive timed release device can be fabricated without reservoir caps. The rate of release of the molecules is thus solely controlled by the physical and material properties of the release system containing the molecule to be delivered. Several possible configurations for passive delivery devices are shown in FIG. 7.

Fabrication of Active Timed Release Reservoir Caps

In a preferred embodiment, photoresist is patterned in the form of electrodes on the surface of the substrate having the reservoirs covered by the thin membrane of insulating or dielectric material. The photoresist is developed such that the area directly over the covered opening of the reservoir is left uncovered by photoresist and is in the shape of an anode. A thin film of conductive material capable of dissolving into solution or forming soluble ions or oxidation compounds upon the application of an electric potential is deposited over the entire surface using deposition techniques such as chemical vapor deposition, electron or ion beam evaporation, sputtering, spin coating, and other techniques known in the art. Exemplary materials include metals such as copper, gold, silver, and zinc and some polymers, as disclosed by Kwon et al. (1991) and Bae et al. (1994). After film deposition, the photoresist is stripped from the substrate. This removes the deposited film, except in those areas not covered by photoresist (lift-off technique). This leaves conducting material on the surface of the substrate in the form of electrodes 360. An alternative method involves depositing the conductive material over the entire surface of the device, patterning photoresist on top of the conductive film using UV or infrared (IR) photolithography, so that the photoresist lies over the reservoirs in the shape of anodes, and etching the unmasked conductive material using plasma, ion beam, or chemical etching techniques. The photoresist is then stripped, leaving conductive film anodes covering the reservoirs. Typical film thicknesses of the conductive material may range from 0.05 to several microns. The anode serves as the reservoir cap and the placement of the cathodes on the device is dependent upon the device's application and method of electric potential control.

An insulating or dielectric material such as silicon oxide ($SiO_x$) or silicon nitride ($SiN_x$) is deposited over the entire surface of the device by methods such as chemical vapor deposition (CVD), electron or ion beam evaporation, sputtering, or spin coating. Photoresist is patterned on top of the dielectric to protect it from etching except on the cathodes and the portions of the anodes directly over each reservoir 380. The dielectric material can be etched by plasma, ion beam, or chemical etching techniques. The purpose of this film is to protect the electrodes from corrosion, degradation, or dissolution in all areas where electrode film removal is not necessary for release.

The electrodes are positioned in such a way that when an electric potential is applied between an anode and a cathode, the unprotected (not covered by dielectric) portion of the anode reservoir cap oxidizes to form soluble compounds or ions that dissolve into solution, exposing the release system containing the molecules to the surrounding fluids. The molecules are released from the reservoir at a rate dependent upon the degradation or dissolution rate of a degradable release system or the rate of diffusion of the molecules out of or through a non-degradable release system. Several possible configurations for active delivery devices are shown in FIG. 8.

Removal of the Insulator Membrane (Reservoir Etch Stop)

The thin membrane of insulating or dielectric material covering the reservoir used as a mask and an etch stop during reservoir fabrication must be removed from the active timed release device before filling reservoir 400 and from the passive timed release device (if the reservoir extends completely through the substrate) after filling reservoir 44. The membrane may be removed in two ways. First, the membrane can be removed by an ion beam or reactive ion plasma. In a preferred embodiment, the silicon nitride used as the insulating material can be removed by a reactive ion plasma composed of oxygen and fluorine containing gases such as $CHF_3$ or $CF_4$. Second, the membrane can be removed by chemical etching. For example, buffered hydrofluoric acid (BHF or BOE) can be used to etch silicon dioxide and hot phosphoric acid can be used to etch silicon nitride.

Reservoir Filling

The release system containing the molecules for delivery is inserted into the large opening of the reservoir by injection, inkjet printing or spin coating 40a/40b/400. Each reservoir can contain a different molecule and dosage. Similarly, the release kinetics of the molecule in each reservoir can be varied by the choice of the release system and cap materials. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. One row may contain a hormone and another row may contain a metabolite. Also, the release system can differ within each row to release a drug at a high rate from one reservoir and a slow rate from another reservoir. The dosages can also vary within each row. For those devices having deep (greater than 10 μm) reservoirs or reservoirs with large (greater than 100 μm) openings, differences in reservoir loading can be achieved by injection or inkjet printing of different amounts of material directly into each reservoir. Variation between reservoirs is achieved in devices having shallow (less than 10 μm) reservoirs, reservoirs that do not pass completely through the substrate, or reservoirs with small (less than 100 μm) openings by a repeated, step-wise process of masking selected reservoirs, spin coating, and etching, as described above regarding the fabrication by spin coating of passive timed release reservoir caps. Preferably, the release system and molecules to be delivered are mixed before application to the reservoirs. Although injection, inkjet printing and spin coating are the preferred methods of filling reservoirs, it is understood that each reservoir can be filled individually by capillary action, by pulling or pushing the material into the reservoir using a vacuum or other pressure gradient, by melting the material into the reservoir, by centrifugation and related processes, by manually packing solids into the reservoir, or by any combination of these or similar reservoir filling techniques.

Device Packaging, Control Circuitry, and Power Source

The openings through which the reservoirs of passive and active devices are filled are sealed by wafer bonding or with a waterproof epoxy or other appropriate material impervious to the surrounding fluids 44/440. For in vitro applications, the entire unit, except for the face of the device containing the reservoirs and electrodes, is encased in a material appropriate for the system. For in vivo applications, the unit is preferably encapsulated in a biocompatible material such as poly(ethylene glycol) or polytetrafluoroethylene.

Figure 3:
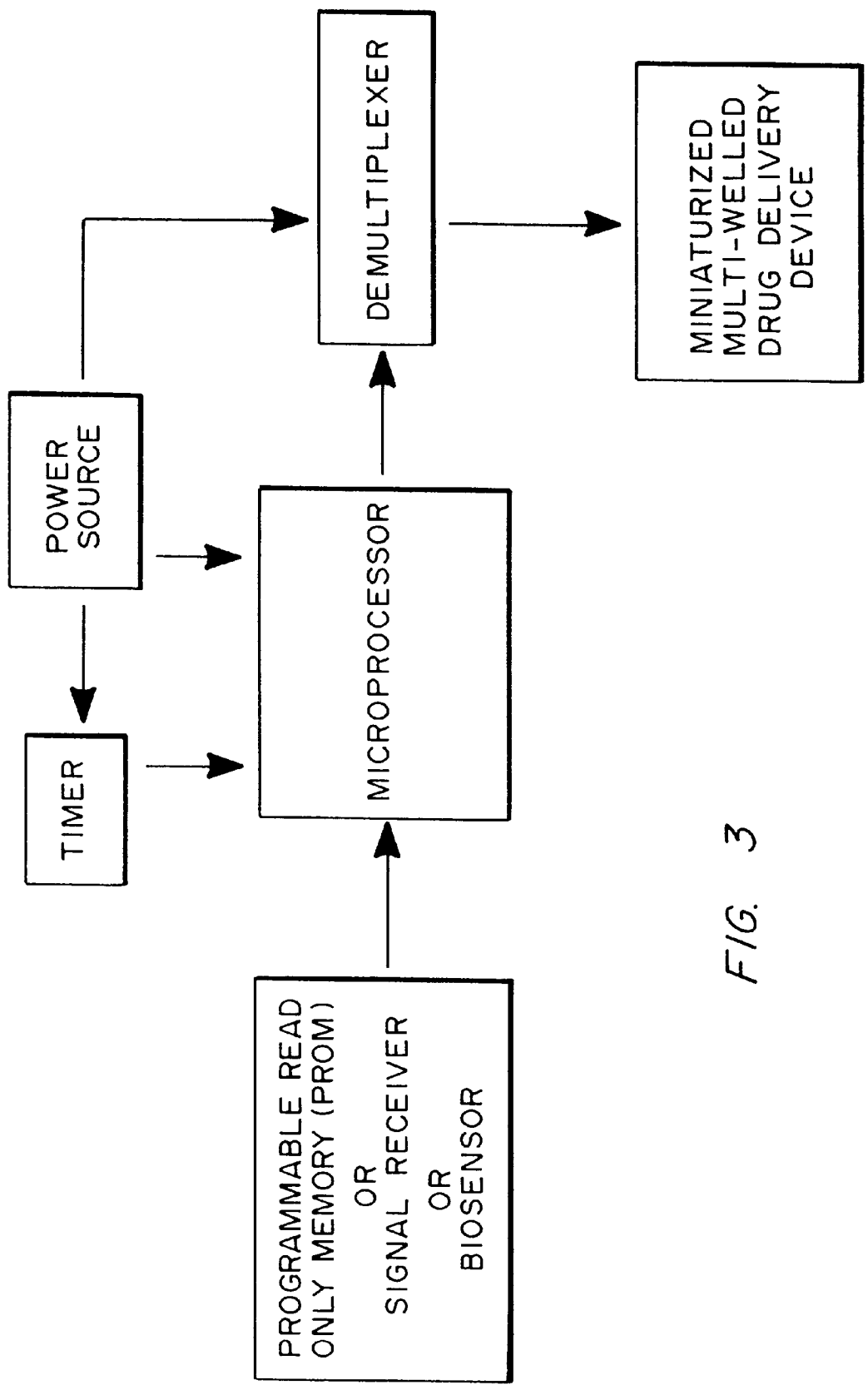
FIG. 3 depicts a typical device control circuitry flowsheet.

The mechanism for release of molecules by the active timed release device does not depend on multiple parts fitted or glued together which must retract or dislodge. Control of the time of release of each reservoir can be achieved by a preprogrammed microprocessor, by remote control, by a signal from a biosensor, or by any combination of these methods, as shown schematically in FIG. 3. First, a microprocessor is used in conjunction with a source of memory such as programmable read only memory (PROM), a timer, a demultiplexer, and a power source such as a microbattery, such as is described, for example, by Jones et al. (1995) and Bates et al. (1992). The release pattern is written directly into the PROM by the user. The PROM sends these instructions to the microprocessor. When the time for release has been reached as indicated by the timer, the microprocessor sends a signal corresponding to the address (location) of a particular reservoir to the demultiplexer. The demultiplexer sends an input, such as an electric potential, to the reservoir addressed by the microprocessor. A microbattery provides the power to operate the PROM, timer, and microprocessor, and provides the electric potential input that is directed to a particular reservoir by the demultiplexer. The manufacture, size, and location of each of these components is dependent upon the requirements of a particular application. In a preferred embodiment, the memory, timer, microprocessor, and demultiplexer circuitry is integrated directly onto the surface of the chip. The microbattery is attached to the other side of the chip and is connected to the device circuitry by vias or thin wires. However, in some cases, it is possible to use separate, prefabricated, component chips for memory, timing, processing, and demultiplexing. These are attached to the backside of the miniaturized delivery device with the battery. The size and type of prefabricated chips used depends on the overall dimensions of the delivery device and the number of reservoirs. Second, activation of a particular reservoir by the application of an electric potential can be controlled externally by remote control. Much of the circuitry used for remote control is the same as that used in the preprogrammed method. The main difference is that the PROM is replaced by a signal receiver. A signal such as radio waves, microwaves, low power laser, or ultrasound is sent to the receiver by an external source, for example, computers or ultrasound generators. The signal is sent to the microprocessor where it is translated into a reservoir address. Power is then directed through the demultiplexer to the reservoir having the appropriate address. Third, a biosensor is integrated into the microchip to detect molecules in the surrounding fluids. When the concentration of the molecules reaches a certain level, the sensor sends a signal to the microprocessor to activate one or more reservoirs. The microprocessor directs power through the demultiplexer to the particular reservoir(s).

Electric Potential Control Methods

The reservoir caps of an active device are anodes that oxidize to form soluble compounds and ions when a potential is applied between the anode and a cathode. For a given electrode material and electrolyte, there exists a range of electric potentials over which these oxidation reactions are thermodynamically and kinetically favorable. In order to reproducibly oxidize and open the reservoir caps of the device, the anode potential must be maintained within this favorable potential range.

There exist two primary control methods for maintaining an electrode within a specific potential range. The first method is called potentiostatic control. As the name indicates, the potential is kept constant during reservoir activation. Control of the potential is typically accomplished by incorporating a third electrode into the system that has a known, constant potential, called a reference electrode. The reference electrode can take the form of an external probe whose tip is placed within one to three millimeters of the anode surface. The potential of the anode is measured and controlled with respect to the known potential of a reference electrode such as a saturated calomel electrode (SCE). In a preferred embodiment of potentiostatic control, a thin film reference electrode and potential feedback controller circuitry could be fabricated directly onto the surface of the microchip. For example, a microfabricated Ag/AgCl reference electrode integrated with a microchip device would enable the device to maintain the anode potential of an activated reservoir within the oxidation regime until the reservoir was completely opened. The second method is called galvanostatic control. As the name indicates, the current is kept constant during reservoir activation. One drawback to this method of control is that there is more than one stable potential for a given current density. However, if the current density versus potential behavior is well characterized for the microchip device in a particular electrolyte system, the current density that will maintain the anode in the oxidation regime will be known. In this case, the galvanostatic method of potential control would be preferable to the potentiostatic control, because galvanostatic control does not require a reference electrode.

MICROCHIP APPLICATIONS

Passive and active microchip devices have numerous in vitro and in vivo applications. The microchip can be used in vitro to deliver small, controlled amounts of chemical reagents or other molecules to solutions or reaction mixtures at precisely controlled times and rates. Analytical chemistry and medical diagnostics are examples of fields where the microchip delivery device can be used. The microchip can be used in vivo as a drug delivery device. The microchips can be implanted into a patient, either by surgical techniques or by injection, or can be swallowed. The microchips provide delivery of drugs to animals or persons who are unable to remember or be ambulatory enough to take medication. The microchips further provide delivery of many different drugs at varying rates and at varying times of delivery.

The methods of fabricating microchip drug delivery devices will be further understood by reference to the following non-limiting examples.

Example 1
Fabrication of Active Release Microchip

1) Obtain double side polished, prime grade, (100) oriented silicon wafers.
  Wafer thickness=approximately 295–310 $\mu$m
2) Deposit approximately 1600–1900 Å of low stress (10:1, silicon rich) silicon nitride on both sides of the wafers in an SVG/Thermco 7000 Series vertical tube reactor (VTR).
  Gas Flows
    Ammonia (NH$_3$)=24 sccm
    Dichlorosilane (SiH$_2$Cl$_2$)=253 sccm
  Temperature=780° C.
  Chamber Pressure=268 mtorr
  Deposition Rate=approximately 30 Å/min.
3) Pattern positive photoresist (PR) as squares (approximately 500 $\mu$m by 500 $\mu$m) serving as the large reservoir openings on one side of the wafers having low stress silicon nitride deposited on them.
  Hexamethyldisilazane deposition on both sides of the wafer ("HMDS vapor prime") in vacuum oven approximately 30 min. at 150° C.
  Photoresist (PR) Type—OCG825–20
  PR Spin Speed and Times (for a Solitec Inc. Model 5110 spinner)
    7 sec. at 500 rpm (coat)
    7 sec. at 750 rpm (spread)
    30 sec. at 3500 rpm (spin)
  Prebake (in Blue M Model DDC-146C oven) 30 min. at 90° C.
  Ultra-violet (UV) exposure for each wafer in the contact alligner (Karl
  Suss Model MA4) with patterned mask
    32 sec. at wavelength=320 nm
  Developer Type—OCG934 1:1
  Put exposed wafers into slightly agitated, room temperature developer
  Develop Time=approximately 40 seconds
  Cascade Rinse=2 min.
  Rinse and Dry Wafers in Spin Rinse Dryer (SRD)
  Postbake (in Blue M Model DDC-146C oven)
    30 min. at 120° C.
4) Etch the VTR nitride to the underlying silicon using a plasma etcher (Plasmaquest Series II Reactor Model 145).
  Gas Flows
    Oxygen (O$_2$)=2 sccm
    Helium (He)=15 sccm
    Carbon Tetrafluoride (CF$_4$)=15 sccm
  Power
    RF=10 W
    ECR=100 W
  Chamber Pressure=20 mtorr
  Temperature=25° C.
  Nitride Etch Rate=approximately 350 Å/min
5) Remove excess PR with solvents—acetone, methanol, isopropanol.
6) Etch the exposed silicon in aqueous potassium hydroxide (KOH) in a wet processing hood (by Semifab, Inc.).
  Concentration=approximately 38–40% by weight
  Temperature=approximately 85–90° C.
  Etch Rate=approximately 1 $\mu$m/min
7) Post-KOH clean in a wet processing hood (by Laminaire Corp.) to avoid K$^+$ contamination in cleanroom.
  Piranha Clean for 15 min.
  Dump Rinse=3 times
  Hydrofluoric Acid (HF) Dip
    10 sec. in 50:1 water:HF solution (by volume)
  Dump Rinse=3 times
  Standard RCA clean
  Rinse and Dry in SRD
8) Pattern image reversal PR over the nitride membranes for subsequent gold liftoff process.
  HMDS vapor prime in vacuum oven approximately 30 min. at 150° C.

Photoresist Type (PR)—AZ 5214 E

PR Spin Speed and Times (for a Solitec Inc. Model 5110 spinner)
   6 sec. at 500 rpm (coat)
   6 sec. at 750 rpm (spread)
   30 sec. at 4000 rpm (spin)

Prebake (in Blue M Model DDC-146C oven)
   30min. at 90° C.

Ultra-violet (UV) exposure for each wafer in the contact alligner (Karl Suss Model MA4) with patterned mask
   40 sec. at wavelength=320 nm Bake for 90 sec. on a metal plate in an oven at 120° C. (Blue M Model DDC-146C)

UV flood exposure for each wafer in the contact alligner (Karl Suss Model MA4) WITHOUT a patterned mask (expose entire wafer)
   Approximately 200 sec. at wavelength=320 nm Developer Type—AZ 422 MIF Put exposed wafers into slightly agitated, room temperature developer
   Develop Time=approximately 1 min. 30 sec.

Cascade Rinse=2 min.

Rinse and Dry Wafers in Spin Rinse Dryer (SRD)

9) Evaporation of gold onto the image revesal PR patterened side of each wafer using a liftoff plate (wafer holder) in an electron beam evaporator (Temescal Semiconductor Products Model VES 2550).
   Gold Deposition Rate=5 Å/sec.
   Gold Thickness=approximately 3000 Å
   Base Pressure=approximately $5.0 \times 10^{-7}$ torr
   Room Temperature (no outside heating or cooling)

10) Liftoff gold layer with acetone.

11) Clean wafers with solvents—acetone, methanol, isopropanol.

12) Oxygen plasma clean (ash) in a plasma etcher (Plasmaquest Series II Reactor Model 145).
   Gas Flows
      $O_2$=25 sccm
      He=15 sccm
   Power
      RF=10 W
      ECR=200 W
   Chamber Pressure=20 mtorr
   Temperature=25° C.

13) Deposit plasma-enhanced chemical vapor deposition (PECVD) silicon dioxide over the entire surface of the wafers having the gold electrodes on them using a PECVD chamber (Plasma—Therm 700 Series Waf'r/Batch Dual Chamber Plasma Processing System).
   Gas Flows
      2% $SiH_4$ in $N_2$=400 sccm
      $N_2O$=900 sccm
   RF Power=20 W
   Chamber Pressure=900 mtorr
   Deposition Rate=approximately 250–500 Å/min.
   Temperature=350° C.

14) Clean wafers with solvents—acetone, methanol, isopropanol.

15) Pattern PR to expose portions of the silicon dioxide covering parts of the gold electrodes.
   HMDS vapor prime in vacuum oven
      approximately 30 min. at 150° C.

Photoresist (PR) Type—OCG825-20

PR Spin Speed and Times (for a Solitec Inc. Model 5110 spinner)
   7 sec. at 500 rpm (coat)
   7 sec. at 750 rpm (spread)
   30 sec. at 3500 rpm (spin)

Prebake (in Blue M Model DDC-146C oven)
   30 min. at 90° C.

Ultra-violet (UV) exposure for each wafer in the contact alligner (Karl Suss Model MA4) with patterned mask
   32 sec. at wavelength=320 nm Developer Type—OCG934 1:1

Put exposed wafers into slightly agitated, room temperature developer
   Develop Time=approximately 55 seconds Cascade Rinse=2 min.

Rinse and Dry Wafers in Spin Rinse Dryer (SRD)

Postbake (in Blue M Model DDC-146C oven)
   30 min. at 120° C.

16) Etch the exposed silicon dioxide to the gold surface with a plasma etcher (Plasmaquest Series II Reactor Model 145).
   Gas Flows
      He=15 sccm
      $CF_4$=15 sccm
   Power
      RF=10 W
      ECR=100 W
   Chamber Pressure=20 mtorr
   Temperature=15° C.
   Silicon Dioxide Etch Rate=approximately 215 Å/min.

17) Spin photoresist on the side of the wafers having the gold electrodes to protect the electrodes during wafer dicing.

Photoresist (PR) Type—OCG825-20

PR Spin Speed and Times (for a Solitec Inc. Model 5110 spinner)
   7 sec. at 500 rpm (coat)
   7 sec. at 750 rpm (spread)
   30 sec. at 3500 rpm (spin)

Prebake (in Blue M Model DDC-146C oven)
   30 min. at 90° C.

18) Dice the wafers with a diesaw (Disco Automatic Dicing Saw Model DAD-2H/6T).
   Process yields 21 devices per 4" wafer with each device measuring 17 mm by 17 mm on a side 19) Etch the nitride membrane from the back of the devices with a plasma etcher (Plasmaquest Series II Reactor Model 145).
   Gas Flows
      $O_2$=2 sccm
      He=15 sccm
      $CF_4$=15 sccm
   Power
      ECR=100 W
   Chamber Pressure=20 mtorr
   Temperature=25° C.
   Nitride Etch Rate=approximately 350 Å/min.

20) Clean the devices with solvents and $O_2$ plasma.
   Solvent clean—acetone, methanol, isopropanol
   Oxygen plasma clean with a plasma etcher (Plasmaquest Series II Reactor Model 145)
   Gas Flows O$_2$=25 sccm
He=15 sccm
Power
  RF=10 W
  ECR=200 W
Chamber Pressure=20 mtorr
Temperature=25° C.
Fabrication of active microchip devices is complete.

Example 2
Fabrication of Passive Release Microchip

1) Obtain double side polished, prime grade, (100) oriented silicon wafers for devices having reservoirs extending completely through the wafer or single side polished, prime grade, (100) oriented silicon wafers for devices having reservoirs that do not extend completely through the wafer.

Wafer thickness=approximately 295–310 μm for devices with reservoirs extending completely through the wafer (devices that do not have reservoirs extending all the way through the wafer can be of any desired thickness)

2) Deposit approximately 1600–1900 Å of low stress (10:1, silicon rich) silicon nitride on both sides of the wafers in an SVG/Thermco 7000 Series vertical tube reactor (VTR).

Gas Flows
        Ammonia (NH$_3$)=24 sccm
        Dichlorosilane (SiH$_2$Cl$_2$)=253 sccm
    Temperature=780° C.
    Chamber Pressure=268 mtorr
    Deposition Rate=approximately 30 Å/min.

3) Pattern positive PR as squares (approximately 500 μm by 500 μm for devices with reservoirs extending completely through the wafer or any desired dimension for devices that do not have reservoirs extending all the way through the wafer) serving as the large reservoir openings on one side of the wafers having low stress silicon nitride deposited on them.

Hexamethyldisilazane deposition on both sides of the wafer
        ("HMDS vapor prime") in vacuum oven approximately 30 min. at 150° C.
    Photoresist (PR) Type—OCG825-20
    PR Spin Speed and Times (for a Solitec Inc. Model 5110 spinner)
        7 sec. at 500 rpm (coat)
        7 sec. at 750 rpm (spread)
        30 sec. at 3500 rpm (spin)
    Prebake (in Blue M Model DDC-146C oven)
        30 min. at 90° C.
    Ultra-violet (UV) exposure for each wafer in the contact alligner (Karl Suss Model MA4) with patterned mask
        32 sec. at wavelength=320 nm
    Developer Type—OCG934 1:1
    Put exposed wafers into slightly agitated, room temperature developer
        Develop Time=approximately 40 seconds
    Cascade Rinse=2 min.
    Rinse and Dry Wafers in Spin Rinse Dryer (SRD)
    Postbake (in Blue M Model DDC-146C oven)
        30 min. at 120° C.

4) Etch the VTR nitride to the underlying silicon using a plasma etcher (Plasmaquest Series II Reactor Model 145).
    Gas Flows
        Oxygen (O$_2$)=2 sccm
        Helium (He)=15 sccm
        Carbon Tetrafluoride (CF$_4$)=15 sccm
    Power
        RF=10 W
        ECR=100 W
    Chamber Pressure=20 mtorr
    Temperature=25° C.
    Nitride Etch Rate=approximately 350 Å/min.

5) Remove excess PR with solvents—acetone, methanol, isopropanol.

6) Etch the exposed silicon in aqueous potassium hydroxide (KOH) in a wet processing hood (by Semifab, Inc.).
    Concentration=approximately 38–40% by weight
    Temperature=approximately 85–90° C.
    Etch Rate=approximately 1 μm/min.

7) Post-KOH clean in a wet processing hood (by Laminaire Corp.) to avoid K$^+$ contamination in cleanroom.
    Piranha Clean for 15 min.
    Dump Rinse=3 times
    Hydrofluoric Acid (HF) Dip
        10 sec. in 50:1 water:HF solution (by volume)
    Dump Rinse=3 times
    Standard RCA clean
    Rinse and Dry in SRD For those devices not having a nitride membrane (reservoirs not extending completely through the wafer), fabrication of passive microchip device is complete. Dice the wafers into individual devices. The reservoirs of each device are ready to be filled.

Alternately, for those devices having a nitride membrane (reservoirs extend completely through the wafer), continue with the following steps.

8) Fill the reservoir using injection, inkjet printing, spin coating or another method with reservoir cap materials, release system, and molecules to be released, or any combination thereof.

9) Seal the reservoir openings on the side of the wafer through which the reservoirs were filled.

10) Etch the nitride membranes on the side of the wafer opposite the filling side by using a plasma etcher (Plasmaquest Series II Reactor Model 145) until the cap material or release system is reached (etch parameters may vary depending on the type of cap material or release system under the nitride).
    Gas Flows
        Oxygen (O$_2$)=2 sccm
        Helium (He)=15 sccm
        Carbon Tetrafluoride (CF$_4$)=15 sccm
    Power
        RF=10 W
        ECR=100 W
    Chamber Pressure=20 mtorr
    Temperature=25° C.
    Nitride Etch Rate=approximately 350 Å/min.

11) Spin photoresist on the side of the wafers having exposed cap materials or release system to protect them during wafer dicing (this step may not be necessary, depending on the type of exposed cap material or release system).
    Photoresist (PR) Type—OCG825-20
    PR Spin Speed and Times (for a Solitec Inc. Model 5110 spinner)
        7 sec. at 500 rpm (coat)
        7 sec. at 750 rpm (spread)

30 sec. at 3500 rpm (spin)

Prebake (in Blue M Model DDC-146C oven)

30 min. at 90° C.

12) Dice the wafers with a diesaw (Disco Automatic Dicing Saw Model DAD-2H/6T).

Process yields 21 devices per 4" wafer with each device measuring 17 mm by 17 mm on a side 13) Clean the devices with solvents and $O_2$ plasma (these steps may not be necessary, depending on the type of exposed cap material or release system).

Solvent clean—acetone, methanol, isopropanol

Oxygen plasma clean in a plasma etcher (Plasmaquest Series II Reactor Model 145)

Gas Flows $O_2$=25 sccm

He=15 sccm

Power

RF=10 W

ECR=200 W

Chamber Pressure=20 mtorr

Temperature=25° C.

fabrication of passive microchip device is complete.

Example 3

Microchip with Passive Timed Drug Release

Figure 4:
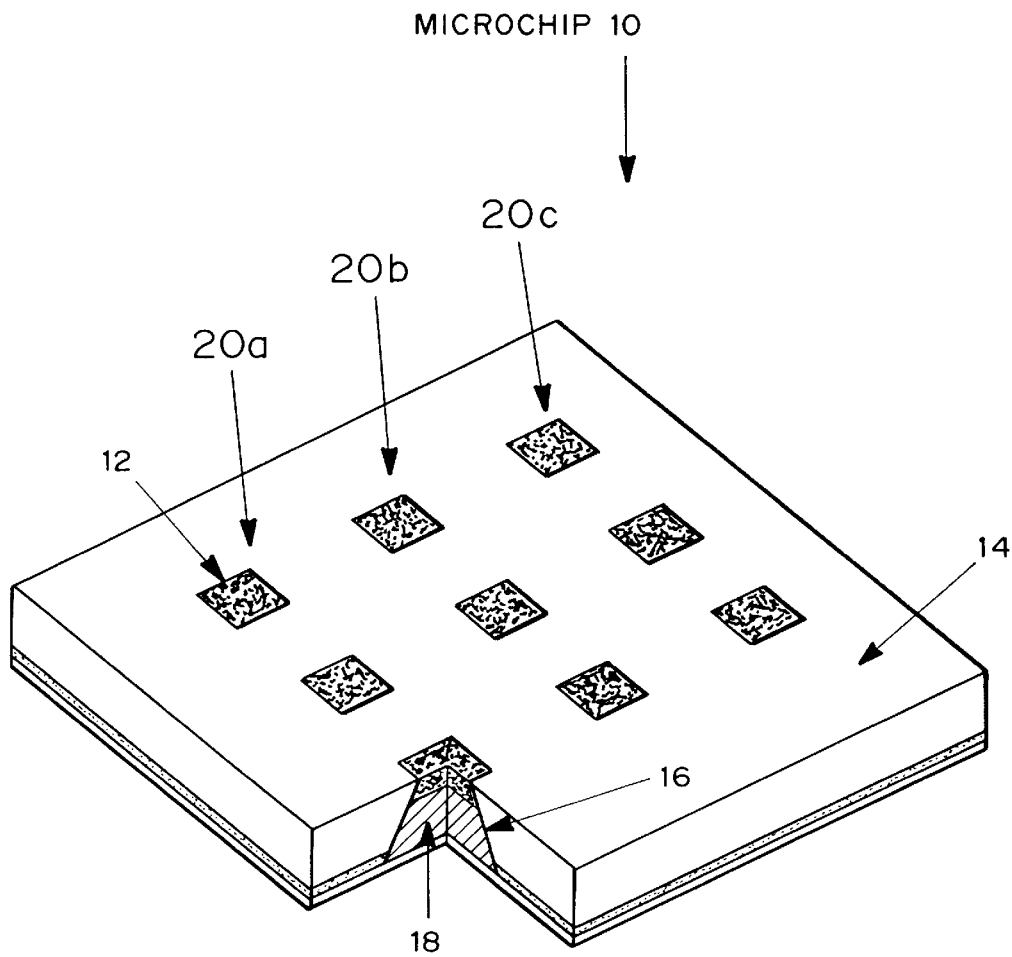
FIG. 4 depicts a passive delivery device.
Figure 4:
Figure 4:
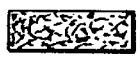
Figure 4:

A passive timed release device, microchip 10 is shown in FIG. 4. Microchip 10 is formed from substrate 14. Reservoirs 16 are etched into substrate 14. Positioned in reservoirs 16 is a release system containing molecules 18 for delivery. The reservoirs are capped with reservoir caps 12. The release system and the molecules for delivery 18 can vary between rows 20a, 20b, 20c, and within reservoirs of each row.

Microchip 10 can be inserted into solution for in vitro applications or be implanted in a selected part of the body for in vivo applications and left to operate without requiring further attention. When exposed to the surrounding fluids, reservoir caps 12 will degrade or become permeable to the release system containing molecules for delivery 18.

Example 4

Microchip with Active Controlled Time Release

Figure 5:
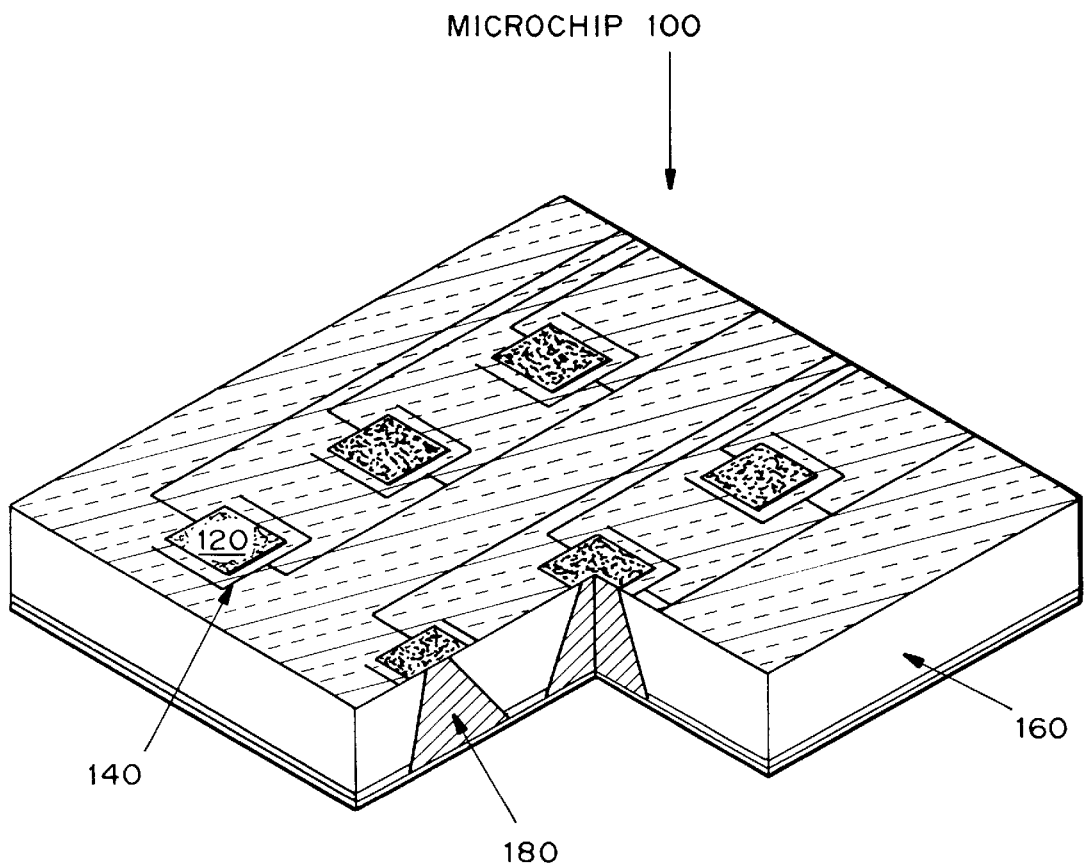
FIG. 5 depicts an active delivery device.

A drug delivery device that provides active timed release is shown as microchip 100 in FIG. 5. Microchip 100 is similar to microchip 10 except that microchip 100 contains electrodes that provide for active timed release. Microchip 100 is formed from substrate 160, release system containing molecules 180 for delivery, anode reservoir caps 120, and cathodes 140. Preferably, microchip 100 further includes an input source, a microprocessor, a timer, a demultiplexer, and a power source (not shown). The power source provides energy to drive the reaction between selected anodes and cathodes. Upon application of a small potential between the electrodes, electrons pass from the anode to the cathode through the external circuit causing the anode material to oxidize and dissolve into the surrounding fluids, exposing the release system containing the molecules for delivery 180 to the surrounding fluids. The microprocessor directs power to specific electrode pairs through a demultiplexer as directed by a PROM, remote control, or biosensor.

Figure 6:
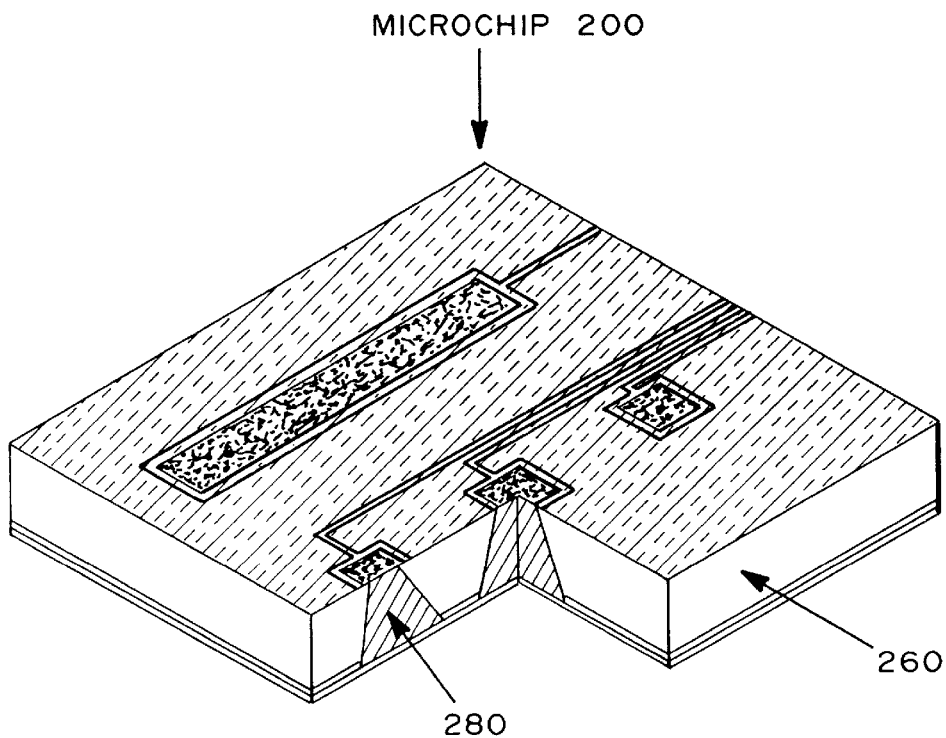
FIG. 6 depicts an active device including insulator overlayers.
Figure 7A:
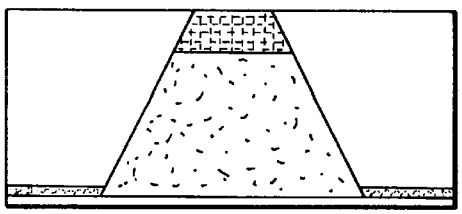
FIGS. 7a–i are schematic views of several configurations of passive delivery devices.
Figure 7E:
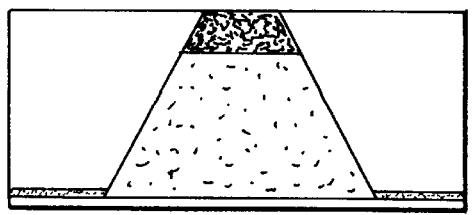
Figure 7B:
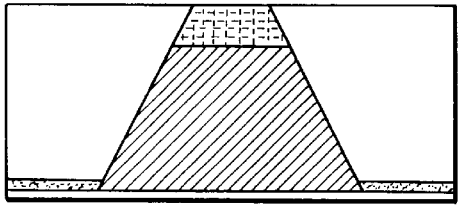
Figure 7F:
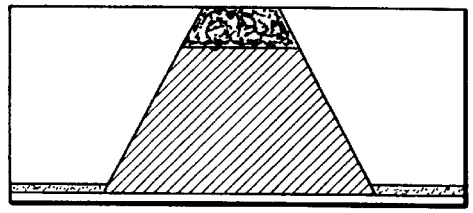
Figure 7C:
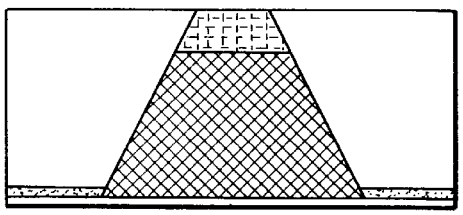
Figure 7G:
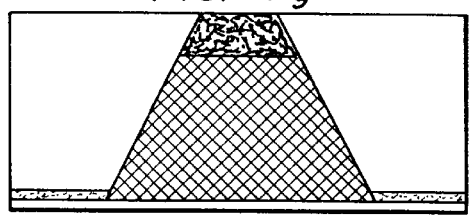
Figure 7D:
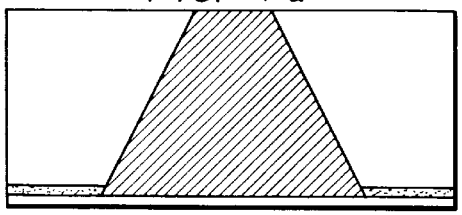
Figure 7H:
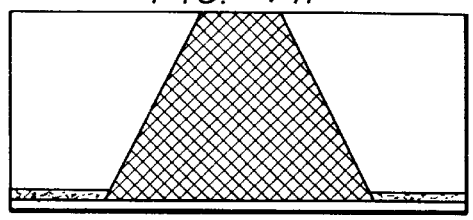
Figure 7I:
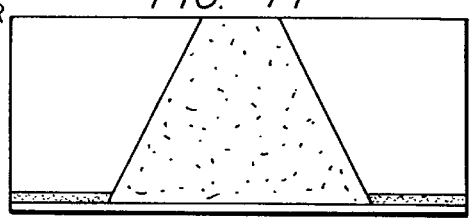
Figure 7I:
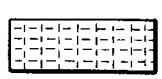
Figure 7I:
Figure 7I:
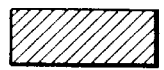
Figure 7I:
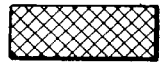
Figure 7I:
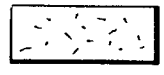
Figure 7I:

Another drug delivery device that provides active timed release is shown as microchip 200 in FIG. 6. Microchip 200, which includes substrate 260 and release system containing molecules 280 for delivery, is similar to microchip 100, but includes different electrode configurations. Microchip 200 illustrates that the shape, size, ratio, and placement of the anodes and cathodes can vary.

We claim:

1. A method of fabricating a microchip device for release of molecules having reservoirs containing the molecules for release comprising:

providing a substrate;

depositing and patterning a material on the substrate for use as an etch mask;

etching a plurality of reservoirs in the substrate;

filling the reservoirs with a release system comprising the molecules; and capping the reservoirs with a cap material which is selectively permeable to the molecules, a cap material which disintegrates to release the molecules, or a combination thereof, thereby forming the microchip device containing within the substrate the molecules to be released.

2. The method of claim 1 wherein the substrate comprises an upper surface and a lower surface, wherein the material for use as an etch mask is deposited onto both the upper surface and the lower surface, and wherein the reservoirs are etched so that the material deposited onto the lower surface serves as a membrane covering each reservoir.

3. The method of claim 1 further comprising filling each reservoir with different types and amounts of cap materials and release systems containing molecules to be delivered.

4. The method of claim 1 wherein the reservoirs are filled by injection, inkjet printing, or spin coating.

5. The method of claim 2 further comprising depositing a thin film of conductive material over the membrane of insulating material covering each reservoir.

6. The method of claim 5 further comprising patterning the conductive film into electrodes so that an anode covers each membrane-covered reservoir opening and cathodes are placed on areas of the device not having reservoirs.

7. The method of claim 6 further comprising depositing a material over each electrode, except the portion of the anode directly over the reservoir and a portion of the cathode.

8. The method of claim 7 further comprising removing the membrane of insulating material from underneath the layer of conductive material covering each reservoir.

9. The method of claim 1 wherein the release system further comprises a biodegradable matrix.

10. The method of claim 1 wherein the cap material is selected from the group consisting of polymers and metals.

11. The method of claim 1 wherein the reservoir cap comprises a UV polymerizable polymer, and the method further comprises exposing the polymer to UV light to selectively crosslink the polymer.

12. The method of claim 1 wherein the molecules are drug molecules.

13. The method of claim 1 wherein the molecules are reagents or diagnostic agents.

* * * * *